United States Patent [19]

Franchi

[11] Patent Number: 5,466,255
[45] Date of Patent: Nov. 14, 1995

[54] PROBE FOR CARDIAC PACEMAKER

[75] Inventor: Pierre Franchi, Vitry/Seine, France

[73] Assignee: ELA Medical, Montrouge, France

[21] Appl. No.: 56,259

[22] Filed: Apr. 30, 1993

[30] Foreign Application Priority Data

Apr. 30, 1992 [FR] France .................................. 92 05356

[51] Int. Cl.⁶ ..................................................... A61N 1/05
[52] U.S. Cl. .......................... 607/128; 607/126; 607/122; 607/119; 128/642
[58] Field of Search ..................................... 607/116, 119, 607/122, 37, 126, 127–132; 128/642

[56] References Cited

U.S. PATENT DOCUMENTS

| | | | |
|---|---|---|---|
| 3,568,660 | 3/1971 | Crites | 128/2 |
| 3,680,544 | 8/1972 | Shinnick | 128/2 R |
| 3,932,656 | 1/1976 | Ramwell et al. | 424/16 |
| 3,978,865 | 9/1976 | Trabucco | 128/419 P |
| 4,011,872 | 3/1977 | Komiya | 128/303.14 |
| 4,033,357 | 7/1977 | Helland et al. | 128/418 |
| 4,055,178 | 10/1977 | Harrigan | 128/260 |
| 4,101,984 | 7/1978 | MacGregor | 3/1.5 |
| 4,144,890 | 3/1979 | Hess | 128/418 |
| 4,711,251 | 12/1987 | Stokes | 128/784 |
| 4,953,564 | 9/1990 | Berthelsen | 128/784 |
| 5,170,802 | 12/1992 | Mehra | 607/126 |

OTHER PUBLICATIONS

Collins, "Implantable Electrode For Critical Locations", *NTIS Tech Notes*, Dec. 1990, p. 1121.

Folkman et al., "Drug Pacemakers In The Treatment of Heart Block", *Annals New York Academy of Sciences*, vol. 167, Art 2, Oct. 30, 1969, pp. 851–868.

*Primary Examiner*—William E. Kamm
*Assistant Examiner*—Kennedy J. Schaetzle
*Attorney, Agent, or Firm*—Davis Hoxie Faithfull & Hapgood

[57] ABSTRACT

A heart signal sensor 11 is connected by a flexible cord 13 to a catheter 17. The sensor 11 and the catheter 17 are attached to install the sensor in the cardiac wall, and thereafter are disunited and separately attached to the cardiac wall 1. The sensor is attached to the cardiac wall by claws projecting from the sensor surface, and may be installed by rotating or by deformation of the sensor.

49 Claims, 6 Drawing Sheets

PROBE FOR CARDIAC PACEMAKER

FIELD OF THE INVENTION

This invention relates to a probe for cardiac pacemaker. Such a probe is comprised of a catheter having at the distal end a sensor with plural electrodes, e.g., at least one detection electrode and one stimulation electrode.

BACKGROUND OF THE INVENTION

The distal end of a cardiac catheter is usually attached to the cardiac wall by a barbed or screw-type catching device to maintain the stimulation and detection electrodes against the cardiac wall. The electrodes are usually disc or ring-shaped, in order to have as much of their area as possible in contact with the cardiac wall. In certain applications, the detection electrodes are separate from the stimulation electrodes and are not in contact with the cardiac wall.

In U.S. Pat. No. 4,365,639, the detection electrodes are arranged on the lateral surface of the catheter, away from the stimulation electrode. In European patent No. 0,191,238, the stimulation electrode is disc-shaped and the detection electrodes are in the shape of a rod having a spherical end that is applied to the cardiac wall via an opening in the stimulation electrode.

In each of the two previous cases, the distal end part of the cardiac probe is practically rigid. In securing the probe to the cardiac wall, the objective is to ensure good contact between the stimulation electrode and the cardiac wall. It is for this reason that the probe is attached efficiently, i.e., traumatically. However, the creation of fibrin and the lesion of the cardiac wall, which modifies the cells, entail a degradation of the stimulation and of the detection. This phenomenon is aggravated by the efforts transmitted by the catheter to the attachment during heartbeats. For instance, the screw-type probe in European patent No. 0,191,238 creates a major lesion.

OBJECTS AND SUMMARY OF THE INVENTION

It is, therefore, an object of the present invention to provide a probe for cardiac pacemaker that may be secured to the cardiac wall with practically no lesion at the electrode-tissue interface. It is another object to separate the electrode-tissue interface site from the site of the lesion resulting from securing the probe catheter to the cardiac wall.

Another object of the present invention is to provide a probe for cardiac pacemaker that may be implanted virtually without any lesion, so that it may be easily moved in the event of improper positioning, or if the implantation tests are unsatisfactory.

A further object of the present invention is to provide a probe for a cardiac pacemaker of which the end sensor is not secured rigidly to the catheter of the probe in order to uncouple it mechanically, so as to enable and enhance the application, i.e., in the best position of the sensor on the cardiac wall, and in order to maintain the sensor, with the minimum of constraints and in a relatively stable position, in intimate contact with the cardiac wall, independently of the movements of the heart.

The present invention broadly concerns a probe for a cardiac pacemaker of the type comprising a heart signal sensor susceptible of applying pacing signals to the heart, and a catheter disposed between said sensor and the pacemaker box, wherein the sensor may be detached from the catheter after having been attached to the cardiac wall.

One aspect of the present invention concerns a probe for cardiac pacemaker comprised of a catheter and a sensor. The sensor will be attached to the cardiac wall. It is located at the distal end of the catheter, and mainly comprises: a support for one or more electrodes, the electrodes being destined to be applied in touching contact with the cardiac wall, and means for attaching the electrode support to the cardiac wall. The electrode support is preferably an insulating board or sheet providing a surface for receiving the electrode or electrodes. Preferably, the sensor is connected to the catheter by a flexible cord through which are run the electrical connections to the electrodes. The insulating board preferably comprises on one side the electrodes and on the other side a block for connection to the flexible cord. Preferably, the block is removably connectable to a tool positionable at the catheter distal end for implantation and extraction of the sensor.

In a preferred embodiment, the sensor comprises means for catching to the cardiac wall distributed over the underside, and preferably around the periphery, of the insulating board. The means for catching the sensor to the cardiac wall are preferably angled claws that are installed by rotation of the sensor. In another embodiment, the catching means of the sensor may be angled claws that are oriented in radial planes containing the axis of the sensor, and installed by deformation of the insulating board, followed by relaxation of the insulating board to its undeformed shape.

In another alternative embodiment, the catching means may be a passive structure such as tines or a fiber mesh, e.g., dacron, which is secured to the insulating board and placed in contact with the heart muscle around part or all of the board periphery, and on which fibrin grows to secure the electrode support board to the cardiac tissue. The fiber may be a biocompatible and/or a biodegradable material.

Preferably, the insulating board electrode support has linear commissures. Preferably, also, the insulating board has a slow-diffusion anti-inflammatory substance around the electrodes.

Another aspect of the present invention concerns a catheter having means for catching to the cardiac wall, wherein said catching means of the catheter are installed by relative displacement in relation to the catheter. Preferably, the catheter catching means provides for securing the catheter to the tissue with the distal end spaced a distance from the tissue.

BRIEF DESCRIPTION OF THE DRAWINGS

Further features and advantages of the invention will be clear from the following detailed description of the invention, with reference to the corresponding accompanying drawings in which.

DETAILED DESCRIPTION OF THE INVENTION

Figure 1:
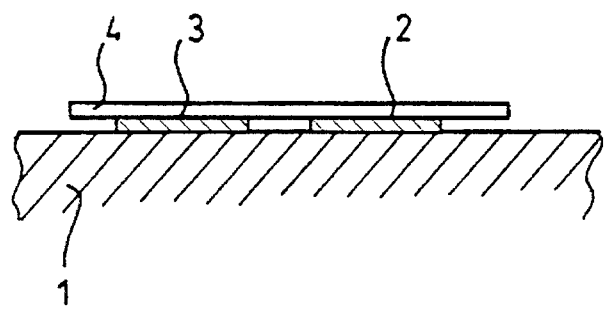
FIG. 1 is a cutaway view of a sample embodiment of a sensor for cardiac pacemaker probe according to an embodiment of the invention.

Referring to FIG. 1, one embodiment of a sensor in accordance with the present invention includes electrodes 2 and 3 secured to the insulating sheet of the electrode support 4 and in contact with the cardiac wall (myocardium) 1. The insulating sheet 4 can be made of a flexible material, e.g. a plastic material. The entire sensor is light and compact. The sensor is thus more respectful of the integrity of the heart muscle with which it will be in contact. The layer of fibrin which forms around the sensor by friction, pressure or traction on the muscle during heart movements is therefore less thick and has little impact on the working of the sensor.

Figure 2:
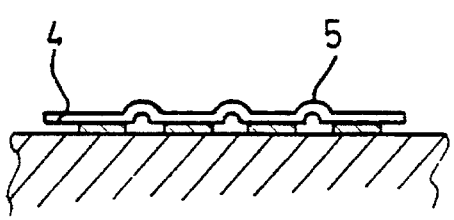
FIGS. 2 and 3 are variations of the embodiment of the sensor in FIG. 1.

In the embodiment of FIG. 2, the electrode support insulating sheet 4 has linear commissures 5, or scores, preferably placed perpendicularly to the contraction direction. The commissures 5 function to make the entire sensor more flexible.

Figure 3:
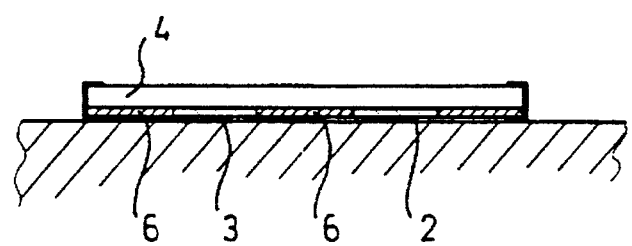

Referring to FIG. 3, the insulating sheet 4 comprises, around the electrodes 2, 3, a slowly diluting anti-inflammatory substance 6 for the purposes of reducing the formation of fibrin. Diffusion of the anti-inflammatory substance is slow, on the one hand, because it can result from a gradual release, but also, on the other hand, because the substance is in a confined area in which there is little or no blood circulation. This is very different from the case of usual electrode type catheters which are swept by the blood flow.

Figure 4:
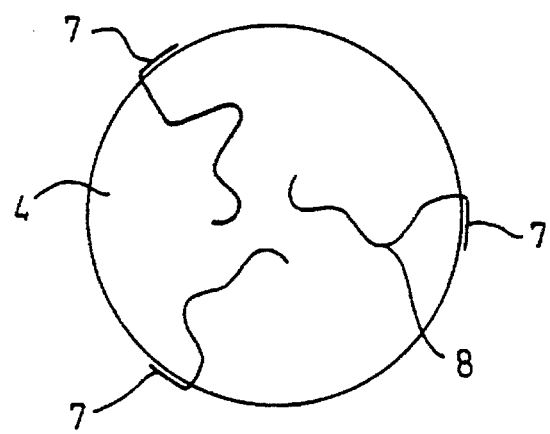
FIG. 4 is a top view showing the attachment system of the sensor embodying the invention.
Figure 5:
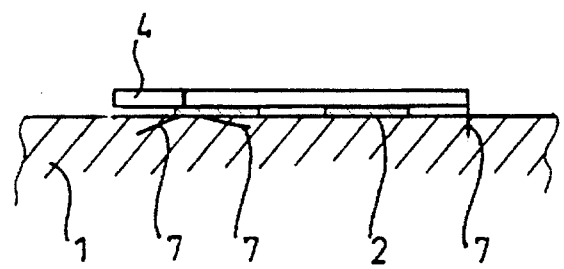
FIG. 5 is a side view of the sensor in FIG. 4.

The catching system for attaching the sensor to the myocardium may be an active means or a passive means. Regarding the active catching means, it mainly comprises claws 7, e.g., 3 in number as illustrated in FIG. 4, distributed around the periphery of the sensor. In the preferred embodiment, the claws 7 are oriented at a tangent to the sensor and at an angle from the plane of the insulating sheet 4. This angle, in the region of 30°, can be seen in FIG. 5. Each claw 7 is extended from an anchoring body 8, of shape appropriate to its function, and preferably situated in the electrode support sheet 4. The anchoring body 8 has at least two parts at an angle from one another and both situated in the sheet 4, so as to lock the claw 7 in position. The anchoring body 8 can have a curved profile in the sheet 4 in order to give it greater rigidity when attaching the sensor to the myocardium. The claws 7 can advantageously be curved, which enhances their penetration by rotation. To ensure that they are maintained in the cardiac wall, the claws 7 preferably have a slight coarseness upon penetration and a greater coarseness as regards extraction. The sensor according to FIGS. 4 and 5 is implanted by a small rotation about its axis, so that the claws 7 penetrate the myocardium during said rotation.

Figure 6:
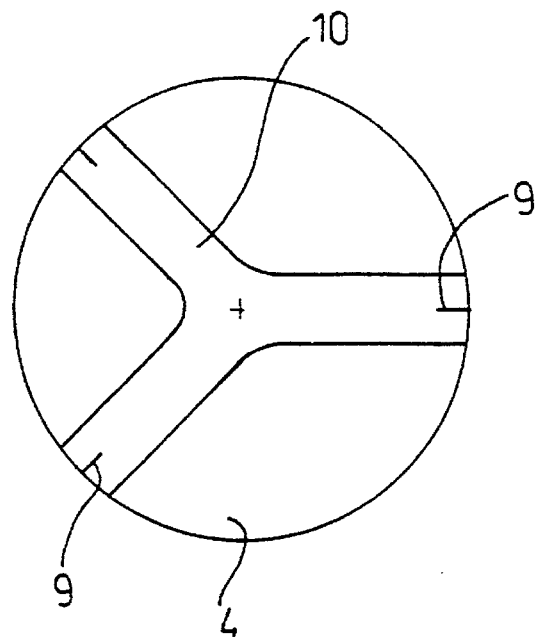
FIG. 6 is a view from below of a variation of the embodiment of the sensor attachment system in FIG. 4.
Figure 7:
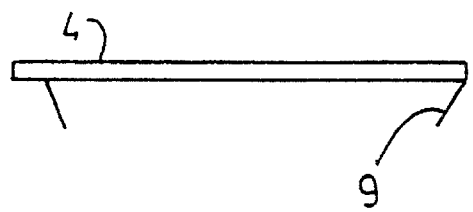
FIG. 7 is a side view of the electrode support in FIG. 6 in the rest position.
Figure 8:
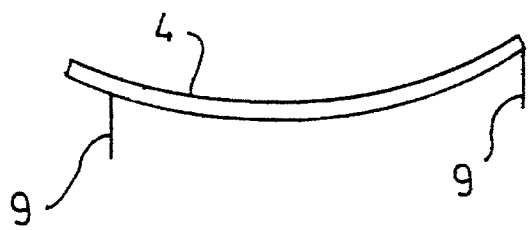
FIG. 8 is a side view of the electrode support in FIG. 7 in the implanted position.

Referring to FIGS. 6–8, an alternate embodiment of a sensor in accordance with the present invention is shown. In FIG. 6, the claws 9 are distributed around the periphery of the sheet 4, and each claw 9 is situated in a radial plane containing the axis of the sensor. In this plane, each claw is inclined on the sheet 4, e.g., at an angle in the region of 70°. In this way, when the sheet 4 is in the rest position, i.e., flat, the claws 9 are inclined in relation to its axis (vertical axis in FIG. 7), and when the sheet 4 is arched (temporarily deformed) for implantation of the sensor on the cardiac wall, the claws 9 are parallel to the axis of the sensor (vertical axis in FIG. 8) for the purposes of easy penetration of the myocardium. Following such penetration (or during penetration when the configuration of the claws 9 permits), the elasticity of the sheet 4 returns it to the undeformed position in FIG. 7.

To ensure the elasticity of the sheet 4, a metal part 10 acting as a spring can be provided on the sheet 4. This metal part 10 can be spoke or star-shaped as represented in FIG. 6.

Figure 9:
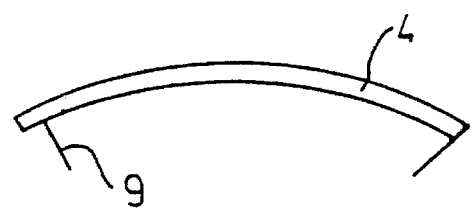
FIG. 9 is a side view of a variation of the embodiment of the electrode support in FIG. 6 in the rest position.
Figure 10:
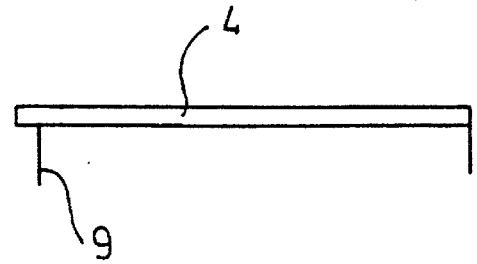
FIG. 10 is a view of the electrode support in FIG. 9 in the implanted position.

In an alternate embodiment, the sheet 4 can be arched in the rest position (as illustrated in FIG. 9) and flat in the implanted position (as illustrated in FIG. 10).

Figure 4A:
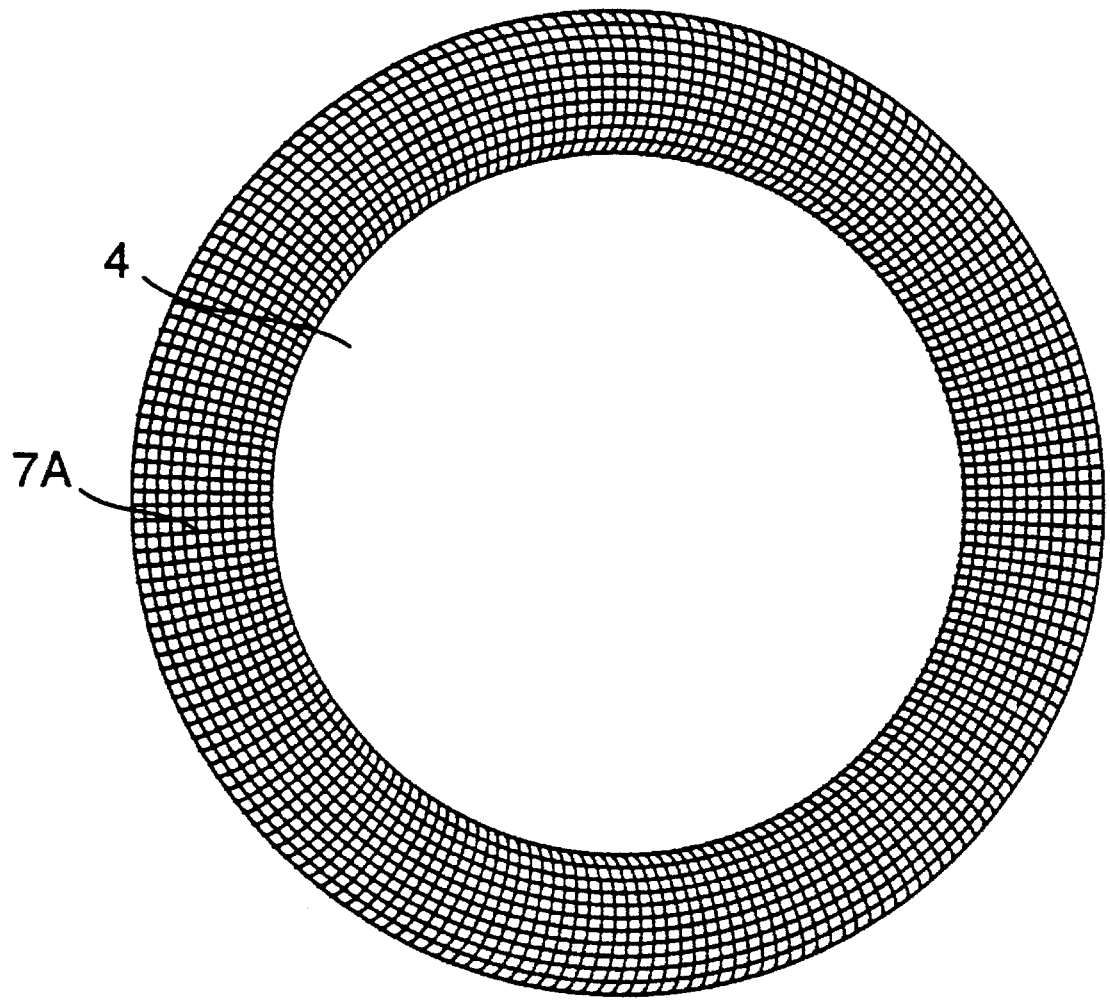
FIG. 4A is a top view showing the attachment system of the sensor embodying the invention having a passive sensor catching means.

In an alternative embodiment, as illustrated in FIG. 4A, the catching means is passive in that it is a material or structure 7A that is placed in contact with the myocardium which facilitates the growth of fibrin over the passive material or structure to secure the sensor to the cardiac tissues without degrading the electrode-tissue interface. The passive catching means 7A may be, for example, a fiber web or mesh around the periphery of the sensor supporting board, or tines extending from the board at a plurality of locations around the board periphery (only the fiber web is shown in FIG. 4A).

Yet another alternative catching means is a hybrid active passive structure that penetrates the tissue to secure the sensor weakly to the tissue and relies on fibrosis to secure the sensor strongly. Such a structure could be made from plastic or metal tines that pass into the tissue, e.g., a short distance or oriented normal to the tissue, and facilitate the growth of fibrin thereon.

Figure 11:
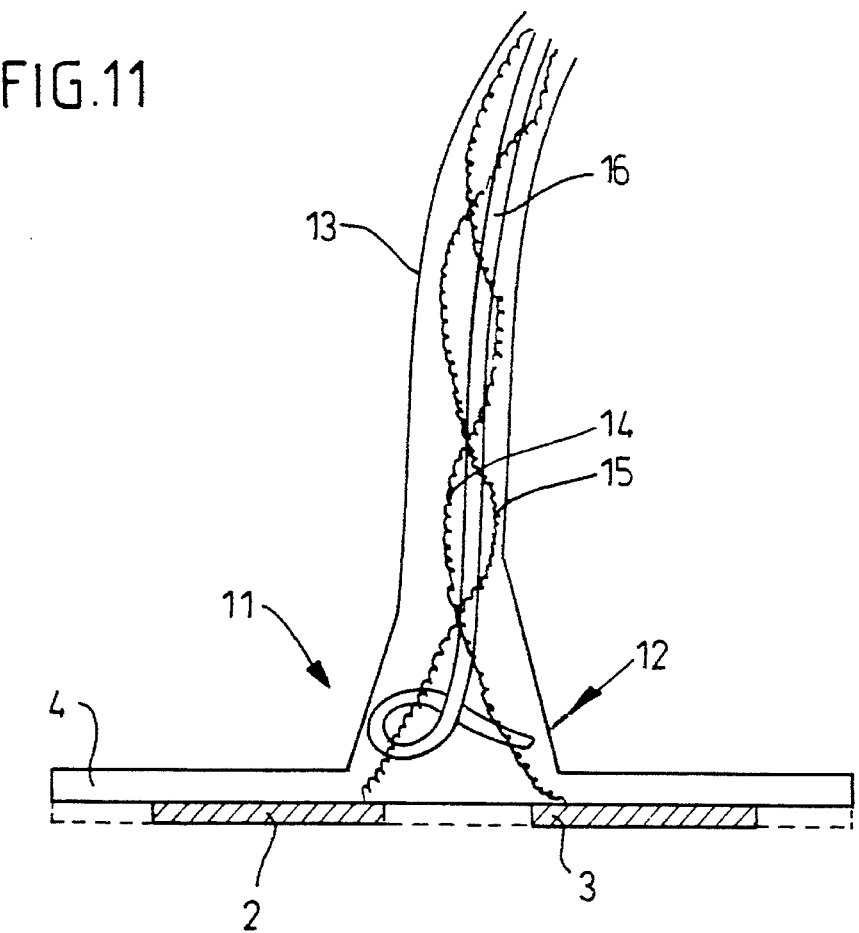
FIG. 11 is a cutaway view of a sensor embodying the invention.
Figure 12:
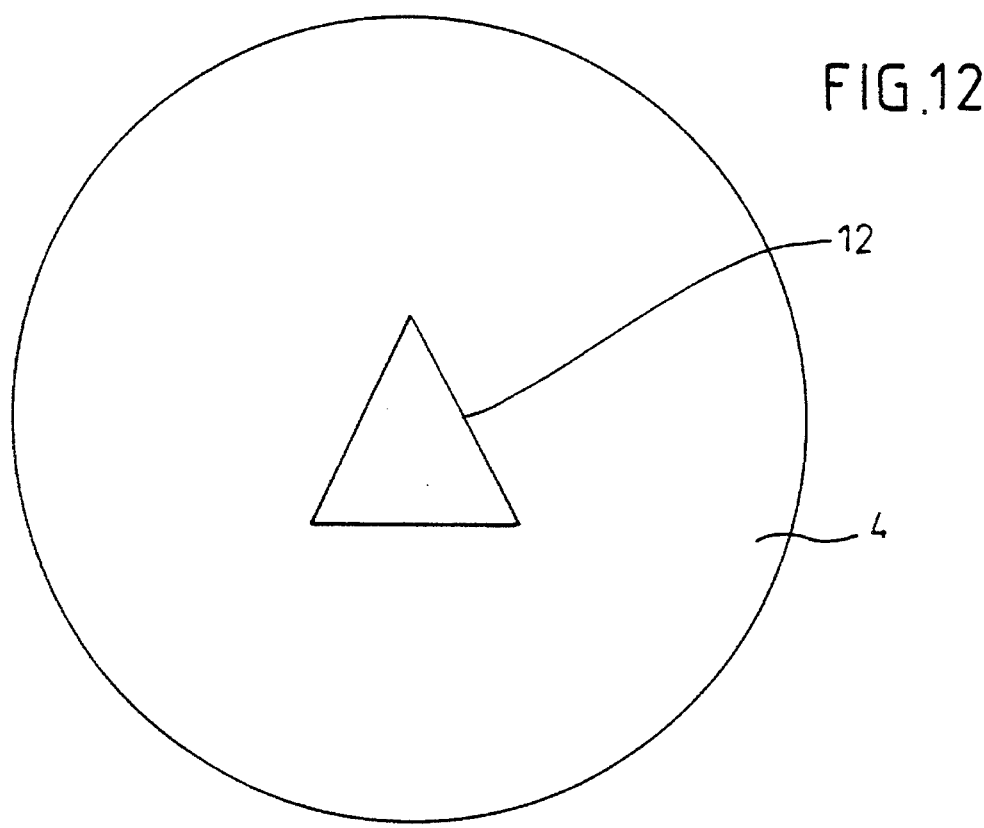
FIG. 12 is a partial top view of the sensor in FIG. 11.

Referring to FIG. 11, a cutaway view of a sensor 11 embodying the invention is shown. This sensor 11 is comprised of the supporting sheet 4 (the sensor catching means is not represented), the electrodes 2, 3, a connection block 12 disposed on the back of the sheet 4, a flexible cord 13 inside which are arranged electrical leads 14, 15 connecting to the electrodes, and an effort recovery cord 16.

In the preferred embodiment, the connection block 12 is shaped, e.g., pyramid-shaped, for the purposes of mating with a corresponding shaped tool 22 capable of performing the rotational maneuvers corresponding to the locking and unlocking of the attachment claws. The shape may be a positive block protrusion from the surface, as illustrated in FIG. 11, or a negative block, e.g., a receptacle in the back surface of board 4. In an alternative embodiment, more than one block 12 may be used such that at least one block is located off-axis to rotate board 4 about an axis of rotation to insert and extract catching means claws. The blocks may be positioned either to protrude from the back surface or to protrude from the side periphery of the sensor (e.g., in opposition about the axis of rotation) and engaged by an approximately shaped tool, e.g., a fork, for rotating the sensor 11.

The electrical leads 14, 15 are preferably comprised of finely spiralled steel, titanium or platinum wires. The effort recovery cord 16 is, e.g., made of a high-resistance plastic material, and is anchored in the connection block 12. The flexible cord 13 is preferably coated with silicon or polyurethane, either by the addition of a sheath, or by duplicate moulding.

Figure 13:
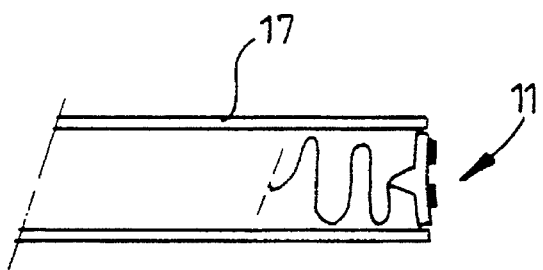
FIG. 13 is a view of the sensor embodying the invention in its catheter.
Figure 14:
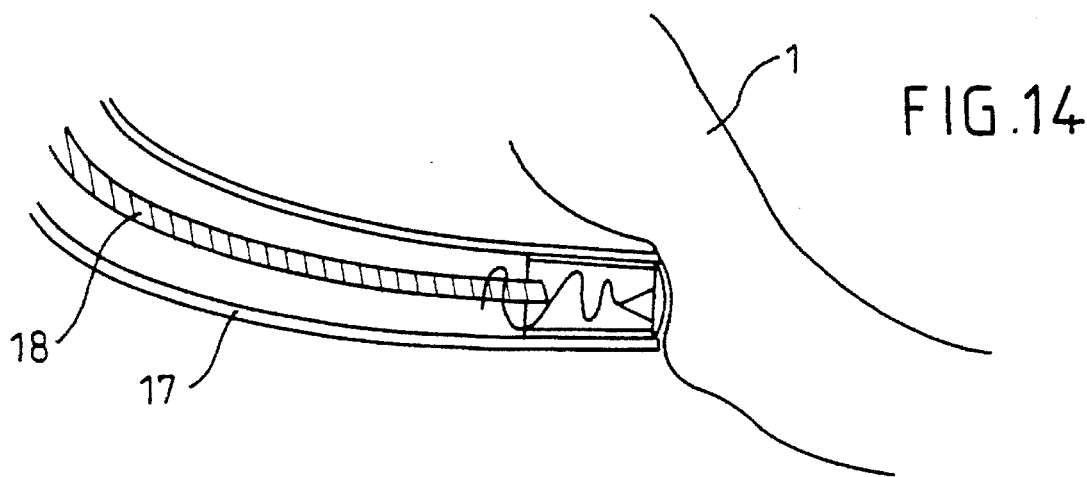
FIG. 14 is a cutaway view showing the sensor being applied to the myocardium (i.e., the cardiac wall) at the time of implantation.

Referring to FIG. 13, a probe embodying the present invention is comprised of a catheter 17 and of the sensor 11. Inside the catheter 17, a guide wire 18 enables the cardiac probe to be guided up until forceful application against the myocardium 1 (FIG. 14) irrespective of the shape of the myocardium facing the sensor 11, and irrespective of the position of the myocardium surface in relation to the axis of the catheter 17. Guide wire 18 contains at its distal end the shaped tool 22 that mates with connection block 12.

The sensor 11 is then attached to the myocardium, either by the claws 7, by rotation of the sensor 11 as commanded by the guide wire 18, or by means of the claws 9 through elastic deformation of the sensor 11, or by fibrin growth over a passive catching means 7A (FIG. 4A). The guide wire 18, when used, may be removed from the catheter 17 following catching the sensor 11 to the tissue.

Figure 15:
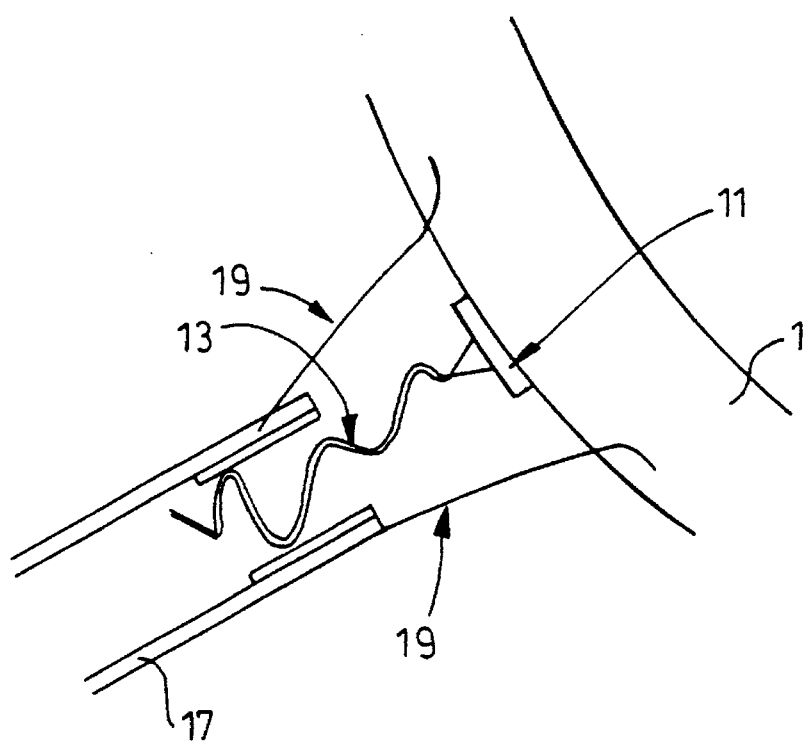
FIG. 15 is a cutaway view showing the disposition of the catheter and the sensor in FIG. 14, in the utilization position.

The catheter 17 is separately attached to the myocardium 1 by a semi-rigid attachment 19 (FIG. 15). The sensor 11 is separated from the catheter 17, and the catheter 17 is withdrawn a distance from the myocardium 1 and maintained in this distant position by the semi-rigid attachment 19. The flexible cord 13 connecting the sensor 11 to the catheter 17 remains free and slack. This arrangement has the advantage of maintaining the sensor 11 applied against the surface of the myocardium without mechanical stress on the part of the catheter 17. The electrodes 2, 3 are thus preserved from any mechanical stress, thereby preserving the performances of the sensor 11 and the electrophysiological characteristics of the myocardium.

Figure 17:
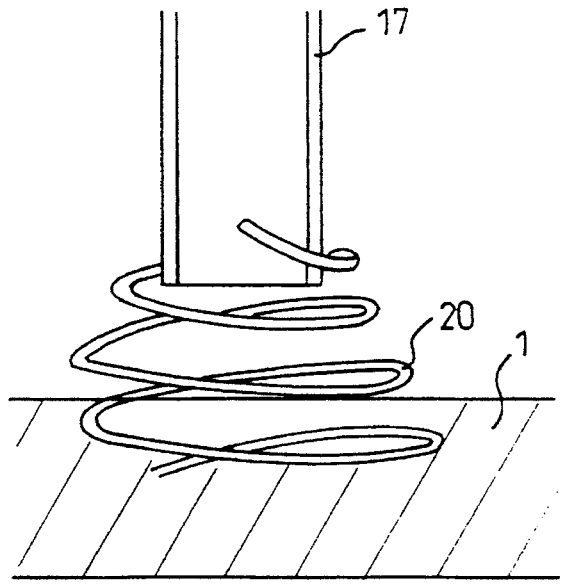
FIG. 17 is a view of the attachment system in FIG. 16 in the unfolded position.
Figure 16:
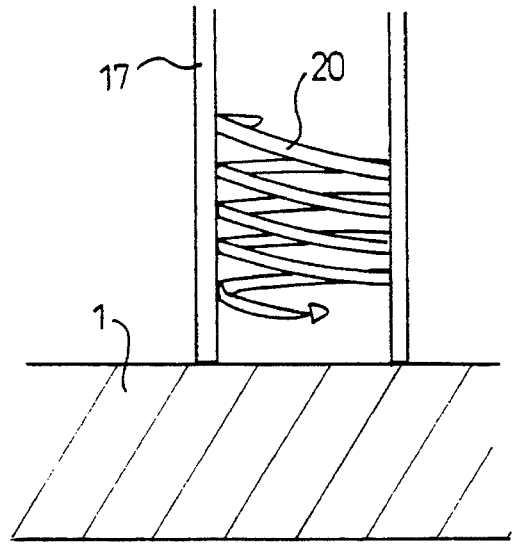
FIG. 16 is a view of a sample embodiment of the catheter attachment system, in the folded position.
Figure 18:
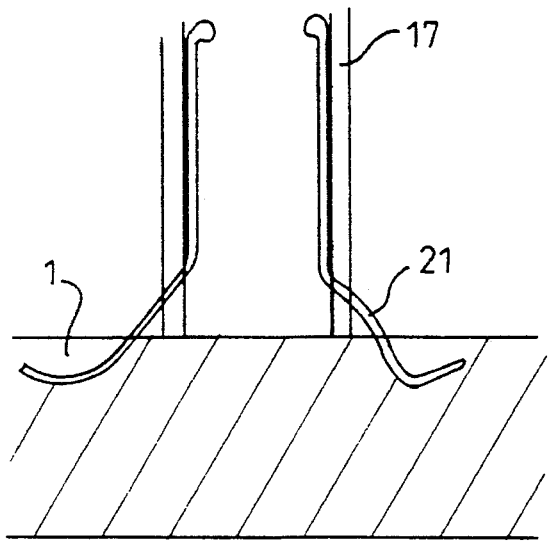
FIG. 18 is a view of another embodiment of the catheter attachment system in the implanted position.
Figure 19:
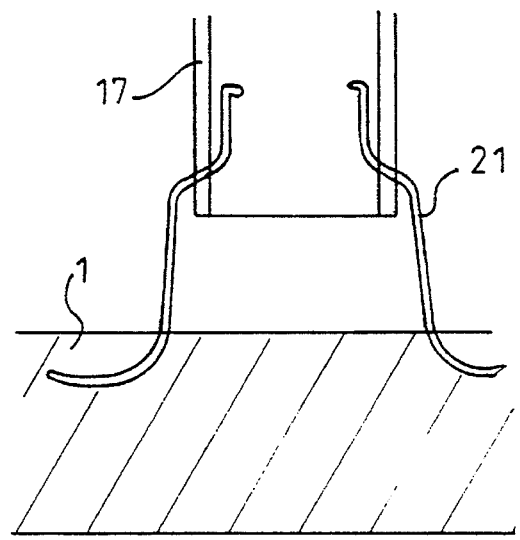
FIG. 19 is a view of the attachment system in FIG. 18, in the utilization position.

The semi-rigid attachment 19 of the catheter 17 can be comprised by a single or multiple helical spring 20 (FIG. 16), extracted from the catheter and winding over a diameter greater than that of the catheter (FIG. 17). A related structure is described in the copending and commonly assigned U.S. patent application Ser. No. 07/812,696, filed Dec. 23, 1991 in the name of Jean-Luc Bens and entitled ENDOCARDIAC LEAD HAVING AN ACTIVE FASTENING MEANS, the disclosure of which is hereby incorporated herein by reference. The attachment 19 alternatively can be comprised of a group of arms 21 which are anchored into the myocardium 1 when the catheter 17 is resting against the myocardium 1 (FIG. 18), which are then unfolded or extended upon withdrawal of the catheter 17, and which are finally locked in relation to the catheter 17 in the withdrawn position of the catheter 17 (FIG. 19).

The attachment system of the catheter 17 and sensor 11 is reversible. By traction on the part of the arms 21 inside the catheter 17 (FIG. 19) or by rotation of the spring 20 (FIG. 17), the catheter 17 approaches the myocardium, the flexible cord 13 re-enters the catheter 17, the catheter is recentered by means of the connection block 12 of the sensor 11, and the sensor 11 is withdrawn from the myocardium. Should this last manoeuvre be hindered by an obstacle, the sensor could be brought back by traction on the flexible connection cord 13, of which the resistance is greater than the tear-off strength of the sensor maintained by the claws and/or fibrin shreds.

The probe embodying the invention has the advantage of implanting the electrodes, borne by the sensor, practically without lesion, and of being able to withdraw them in the event of improper positioning, or if the implantation tests are not satisfactory, or at a later stage if the sensor needs to be withdrawn due to infection, or to displace it because the area at which it is applied has lost its activity, e.g. in the event of infarct. Furthermore, the sensor is of very small dimensions, and can be implanted equally well in a ventricle or in an atrium, practically without lesion of the myocardium.

The electrodes are preferably thin and light conductive plates, e.g. produced in the form of metal or carbon deposits.

Another advantage of the sensor of the present invention is that more than two electrodes can be used in a given sensor. This will provide for following cardiac activity at the cellular level for determining the vector of cardiac electrical activity and to monitor better myocardial cellular activity. For example, it is envisaged that at least one sensing electrode and two pacing electrodes can be used in the same sensor, with the result that a lower threshold stimulating pulse energy will be needed to depolarize the heart cells to start a contraction. It also is envisaged that it will be possible to detect the vector of cardiac electrical activity to understand and control better pacing activity and minimize the delivery of stimulation pulses.

One skilled in the art will appreciate that the present invention can be practiced by other than the disclosed embodiments which are presented for the purposes of illustration and not of limitation.

I claim:

1. A probe for a cardiac pacemaker comprising a heart signal sensor susceptible of applying pacing signals, a catheter having a distal end disposed between said sensor and the pacemaker and a flexible cord connected to said sensor and said catheter, and a semi-rigid attachment having a first end connected to the catheter and a second end for attachment to a cardiac wall, wherein the sensor is united with the catheter distal end for attachment to a cardiac wall and after said attachment the catheter distal end is disunited from said sensor and maintained at a distance from said sensor with the catheter connected to said sensor by the flexible cord and connected to the cardiac wall by the semi-rigid attachment so as not to apply any mechanical stress on said sensor.

2. The probe as claimed in claim 1, wherein said sensor further comprises an electrode and the catheter further comprises an electrical conductor electrically connected to the electrode, said electrical conductor being passed through the flexible cord.

3. The probe as claimed in claim 2, wherein said sensor comprises an insulating board comprising on one side said electrode and on the other side a block for connection to said flexible cord.

4. The probe as claimed in claim 3, wherein said insulating board has a commissure.

5. The probe as claimed in claim 3, wherein said insulating board has a slow-diffusion anti-inflammatory substance around said electrode.

6. The probe as claimed in claim 3, wherein said sensor comprises means for catching to said cardiac wall distributed over said other side of said insulating board.

7. The probe as claimed in claim 6, wherein said means for catching the sensor to the cardiac wall are angled claws and are installed by rotation of said sensor.

8. The probe as claimed in claim 6, wherein said sensor catching means are angled claws situated in radial planes containing the axis of said sensor, and are installed by deformation of said insulating board.

9. The probe as claimed in claim 6, wherein said sensor catching means is a passive structure for promoting fibrin growth to secure the sensor to the cardiac wall.

10. The probe of claim 2 wherein said electrode further comprises at least two electrodes and said flexible cord comprises at least two electrical leads connected to said at least two electrodes respectively, said electrical leads running therethrough to connect electrically said electrodes to said catheter electrical conductor.

11. The probe as claimed in claim 1, wherein said semi-rigid attachment comprises means for catching to said cardiac wall.

12. The probe as claimed in claim 1, wherein said semi-rigid attachment first end is movable in relation to said catheter to install said semi-rigid attachment second end in the cardiac tissue.

13. A method of connecting a cardiac pacemaker electrode to cardiac tissue comprising:
(a) providing a sensor having an electrode and a catheter having a sensor receptacle at the distal end;
(b) mating the sensor to the sensor receptacle of the catheter;
(c) positioning the catheter distal end so that the sensor electrode is in contact with the cardiac tissue;
(d) securing the sensor to the cardiac tissue;
(e) separating the sensor from the sensor receptacle; and
(f) securing the catheter to the cardiac tissue at a distance from the sensor so that the catheter does not apply any significant mechanical stress on the sensor.

14. The method of claim 13 wherein step (a) further comprises providing the sensor with an insulating board on which the electrode is secured, mounting a plurality of claws on the insulating board to project at an angle from the insulating board, and wherein step (d) further comprises manipulating the claws to pass into the tissue.

15. The method of claim 14 wherein the insulating board has an axis of rotation and the plurality of claws extend from the board and step (d) further comprises rotating the insulating board so that the claws pass into the tissue.

16. The method of claim 15 further comprising providing the sensor with a slow-diffusion anti-inflammatory substance around the electrodes.

17. The method of claim 14 wherein the insulating board is deformable and has an undeformed shape and the plurality of claws extend from the board wherein step (d) further comprises deforming the board and moving the board towards the tissue so that the claws pass into the tissue, and allowing the board to return to its undeformed shape.

18. The method of claim 17 further comprising providing the sensor with a slow-diffusion anti-inflammatory substance around the electrodes.

19. The method of claim 14 wherein step (b) further comprises providing the insulating board with a shaped-block and inserting the block in the sensor receptacle.

20. The method of claim 14 further comprising connecting the sensor to the catheter by a flexible cord containing an electrical connection between the electrode and the cardiac pacemaker.

21. The method of claim 20 further comprising withdrawing the electrode from the cardiac tissue by remating the sensor with the sensor receptacle and manipulating the sensor to withdraw the claws from the tissue.

22. The method of claim 14 further comprising connecting the sensor to a recovery cord for pulling the sensor secured to tissue away from the tissue.

23. The method of claim 13 wherein step (a) further comprises providing the sensor with an insulating board on which the sensor is secured, providing the insulating board with a passive structure for promoting fibrin growth thereon, and wherein step (d) further comprises placing the passive structure in contact with the cardiac tissue for a time to permit fibrin to grow and secure the electrodes in contact with the cardiac tissue.

24. A probe for connecting a cardiac pacemaker to cardiac tissue for monitoring and stimulating cardiac activity comprising:
a sensor having an electrode and means for catching the sensor to the cardiac tissue;
a catheter interposed between the pacemaker and the cardiac tissue having a distal end; and
means for securing the catheter to the cardiac tissue with the distal end spaced a distance from the sensor so as not to apply any mechanical stress on the sensor.

25. The probe of claim 24 wherein the catheter further comprises a passageway and the sensor further comprises an electrode and a wire connecting the electrode to the pacemaker and passing through the catheter passageway.

26. The probe of claim 24 wherein the sensor further comprises:
an insulating board having first and second sides, the electrode being mounted on one side of the insulating board; and
a shaped-block mounted on the other side of the insulating board, wherein the catheter distal end has an aperture for receiving the sensor shaped-block.

27. The probe of claim 24 wherein the sensor catching means further comprises a plurality of claws, the claws being oriented for insertion into the cardiac tissue to hold the electrode in contact with the cardiac tissue.

28. The probe of claim 27 wherein the plurality of claws are mounted on the insulating board and project from the insulating board on the one side of the insulating board.

29. The probe of claim 28 wherein the plurality of claws project tangentially to the periphery of the insulating board so that the claws may be inserted into cardiac tissue by rotation of the sensor.

30. The probe of claim 28 wherein the insulating board has an axis and is deformable about the axis and the plurality of claws project in radial planes containing the axis the insulating board so that the claws may be inserted into the cardiac tissue by deforming the insulating board.

31. The probe of claim 24 wherein the means for securing the catheter further comprises a spring that is inserted into the cardiac tissue by rotation relative to the catheter.

32. The probe of claim 24 wherein the sensor further comprises an insulating board on which the electrode is mounted and the insulating board further comprises a commissure.

33. The probe of claim 24 wherein the sensor further comprises an insulating board on which the electrode is mounted and the insulating board further comprises a slow diffusion anti-inflammatory substance proximate to said electrodes.

34. A probe for connecting a muscle stimulating device to muscle tissue comprising:

a catheter disposed between the stimulating device and the muscle tissue having an interior passageway and means for securing the catheter to the muscle tissue at a distance from the tissue; and a sensor comprising:
an insulating sheet,
an electrode mounted on the insulating sheet,
a wire electrically connecting the electrode to the muscle stimulating device and passing through the catheter passageway, and
a plurality of claws projecting from the insulating sheet oriented to penetrate and secure the sensor electrode to the muscle tissue independent of the catheter, wherein the secured catheter does not apply any substantial mechanical stress on the secured sensor.

35. The probe of claim 34 wherein the sensor further comprises a source of slow diffusing anti-inflammatory substance proximate to said electrodes.

36. The probe of claim 34 wherein the sensor further comprises a block and a flexible cord connecting the sensor to the probe, wherein the catheter further comprises a sensor receptacle for receiving the block for securing the sensor to the cardiac wall.

37. The probe of claim 36 wherein the catheter further comprises a guide wire secured to the sensor receptacle for rotating the sensor to secure the sensor to the cardiac wall.

38. The probe of claim 36 wherein the sensor further comprises a spring for biasing the sensor in an undeformed shape.

39. A probe for a cardiac pacemaker comprising a heart signal sensor susceptible of applying pacing signals, a catheter disposed between said sensor and the pacemaker, a flexible cord connecting the sensor to the catheter, and semi-rigid attachment element connected to the catheter and installable in a cardiac wall wherein said sensor further comprises an electrode to contact a cardiac wall, the flexible cord further comprises an electrical conductor electrically connected to the electrode, and the catheter is disunitable from said sensor and attachable to the cardiac wall by said semi-rigid attachment element so that the catheter is maintained at a distance from said sensor and does not apply any mechanical stress on the sensor when said sensor is attached to the cardiac wall and the catheter is attached to the cardiac wall by said semi-rigid attachment element.

40. The probe as claimed in claim 39, wherein said sensor comprises an insulating board comprising on one side said electrode and on the other side a block for connection to said flexible cord.

41. The probe as claimed in claim 40, wherein said insulating board has a commissure.

42. The probe as claimed in claim 40, wherein said insulating board has a slow-diffusion anti-inflammatory substance around said electrode.

43. The probe as claimed in claim 40, wherein said sensor comprises means for catching to said cardiac wall distributed over said other side of said insulating board.

44. The probe as claimed in claim 43, wherein said means for catching the sensor to the cardiac wall are angled claws and are installed by rotation of said sensor.

45. The probe as claimed in claim 43, wherein said sensor catching means are angled claws situated in radial planes containing the axis of said sensor, and are installed by deformation of said insulating board.

46. The probe as claimed in claim 43, wherein said sensor catching means is a passive structure for promoting fibrin growth to secure the sensor to the cardiac wall.

47. The probe as claimed in claim 39, wherein said semi-rigid attachment element comprises means for catching to said cardiac wall.

48. The probe as claimed in claim 39, wherein said semi-rigid attachment element is movable in relation to said catheter to install said semi-rigid attachment element in said cardiac wall.

49. The probe as claimed in claim 39 wherein said electrode further comprises at least a first electrode and a second electrode and said flexible cord comprises at least two corresponding electrical conductors running therethrough to connect electrically said first and second electrodes respectively to said pacemaker.

* * * * *